United States Patent [19]
Register

[11] Patent Number: 5,827,545
[45] Date of Patent: Oct. 27, 1998

[54] VETERINARY PHARMACEUTICAL COMPOSITION AND METHOD OF ADMINISTRATION

[76] Inventor: Jack W. Register, 1513 5TH Ave., East, Menomonie, Wis. 54751

[21] Appl. No.: 599,021

[22] Filed: Feb. 8, 1996

[51] Int. Cl.[6] .......................... A61K 33/06; A61K 33/14
[52] U.S. Cl. .......................... 424/678; 424/679; 424/681
[58] Field of Search .................................... 424/602, 678, 424/679, 681

[56] References Cited

U.S. PATENT DOCUMENTS

| | | |
|---|---|---|
| 3,606,085 | 9/1971 | Spilman . |
| 4,001,445 | 1/1977 | Horrocks et al. ...................... 426/250 |
| 4,020,838 | 5/1977 | Phillips et al. . |
| 4,033,346 | 7/1977 | Phillips et al. . |
| 4,040,422 | 8/1977 | Kuhn . |
| 4,073,293 | 2/1978 | Phillips et al. . |
| 4,245,757 | 1/1981 | Phillips et al. . |
| 4,359,050 | 11/1982 | Reynolds . |
| 4,406,654 | 9/1983 | Bristow . |
| 4,425,121 | 1/1984 | Young et al. . |
| 4,439,337 | 3/1984 | Nimerick et al. ......................... 252/70 |
| 4,601,909 | 7/1986 | Nagoshi ................................. 426/524 |
| 4,898,781 | 2/1990 | Onouchi et al. ................... 428/402.22 |
| 5,139,488 | 8/1992 | Klein . |
| 5,154,324 | 10/1992 | Stratford . |
| 5,162,580 | 11/1992 | Gancy ..................................... 562/607 |
| 5,176,645 | 1/1993 | Guerrero . |
| 5,188,610 | 2/1993 | Rains . |
| 5,264,269 | 11/1993 | Kakiuchi et al. ........................ 428/156 |
| 5,342,624 | 8/1994 | McNeill et al. . |
| 5,556,634 | 9/1996 | Moore ..................................... 424/438 |

OTHER PUBLICATIONS

Goff et al. "Calcium Salts for Treating Hypocalcemia: Carrier Effect Acid–Base Balance, and Oral Versus Rectal Administration", Journal of Dairy Science, vol. 77, No. 4 (Apr. 1994).

*Primary Examiner*—Jeffrey C. Mullis
*Attorney, Agent, or Firm*—Skinner and Associates

[57] ABSTRACT

A composition for preventing and treating milk fever in freshening cows, and a method of administering the composition. The basic composition is a mixture of water, calcium chloride, propylene glycol, B vitamins and minerals. The calcium content of 25 grams per dose is lower than conventional calcium treatments used for this purpose. The propylene glycol gives the cow an energy boost and sweetens the taste so the cow does not object to it as it does to conventional gels and liquids. The B vitamins stimulate the cow's appetite. The minerals replace minerals lost in the milk and also help calcium absorption. The composition of the present invention is in a liquid form and is preferably administered using a 200 cc drench gun. The end of the dispensing tube of the drench gun is placed between the teeth and cheek of the cow and inserted all the way to the back of the cheek. A feature near the end of the dispensing tube causes a bulge in the cow's cheek which indicates the position of the dispensing tube from outside of the cow's mouth. The cow swallows the liquid mixture in a near normal manner which prevents the solution from being inhaled and causing aspiration pneumonia. The minimal irritation of the solution in the cow's throat allows the esophageal groove to open, thereby allowing the liquid into the omasum where absorption is faster than in the rumen where most of the other compositions for this purpose end up.

11 Claims, 2 Drawing Sheets

VETERINARY PHARMACEUTICAL COMPOSITION AND METHOD OF ADMINISTRATION

BACKGROUND OF THE INVENTION

1. Field of the Invention.

The present invention relates, generally to veterinary pharmaceutical and feed supplement compositions and methods of administering them. More particularly, the invention relates to a composition of calcium, B-vitamins and propylene glycol and a method of administering the composition to dairy cattle by injection at a predetermined location in the mouth of such animals.

2. Background Information.

The process of a cow giving birth to a calf is called "freshening" in the dairy industry. Low serum calcium levels in the blood of freshening cows can cause hypocalcemia, commonly referred to as milk fever. Even though freshening cows do not show symptoms of milk fever, i.e. staggering and cold ears, they may sill have subclinical milk fever, which is typically asymptomatic. The normal level of serum calcium in a cow's blood is 9.0 mg/100 cc of blood. Subclinical milk fever occurs when the level drops below 7.5 mg. At 6.0 mg, the rumen shuts down. At 4.0 mg the cow is down.

In a fresh cow, the first milk, or colostam, has a high level of calcium and antibodies to benefit the newborn calf's immune system. But the calf does not enjoy the full benefit of its mother's milk because in today's dairy industry it is not practical to allow a fresh cow to go a long period of time without milking. During calving and when a cow is milked after freshening, it loses that high level of calcium, which the cow has to replace. The replacement calcium comes from the bloodstream, which makes the cow vulnerable to milk fever or subclinical milk fever.

Other problems related to low serum calcium levels are displaced abomasum, slow calving, and retained placenta, ketosis, downer cow syndrome, uterine prolapse, and metritis.

Milk fever and the other problems associated with low serum calcium can be prevented in freshening cows by keeping serum calcium in the blood at or above the level of 7.5 mg/100 cc of blood.

In the past, various devices and/or methods have been used to raise serum calcium levels in freshening cows. These include intravenous dosing, gel tube solutions placed into the mouth with a caulking gun, and liquid solutions poured into the cow's mouth from a bottle. However, these devices and methods have significant limitations and shortcomings, specifically the following.

Intravenous dosing (IV) is generally administered by a veterinarian. It is time consuming due to the importance of a slow administration rate. It also tends to spike the blood with a large amount of calcium to which the cow responds by releasing a hormone called calcitonin that temporally shuts down all mechanisms that allow the cow's body to restore calcium. When the IV calcium is gone, relapse can occur within 12 hours after treatment. Thus, IV dosing tends to be a temporary solution and, therefore, is not good for milk fever prevention. Furthermore, IV treatments are a shock to the system and can cause stress to the animal and even death.

Gel tubes do not require a veterinarian to administer them, but they are generally difficult to administer. The gel is forced from a caulking gun and is placed over the cow's tongue. In a 300 cc dose, gel tubes contain about 50 grams of calcium in the form of 150–200 grams of calcium chloride, which gives the gel a harsh salty taste. A cow does not like to have a tube of bad tasting gel forced into its mouth, so it fights the product being forced over its tongue. If the tube does get in, the cow's natural reflexes to cough out the bad tasting substance results in much of the gel being spit out. Furthermore, the high levels of calcium chloride in the gel can cause acidosis and also irritate the throat which can restrict multiple feedings if one feeding has no results. Administering the gels gets the animal excited, and it has been shown that in an excited animal the calcium absorption is lowered.

Another problem with gels administered over the tongue, as well as with liquids described below, is that cow can inhale the product into its lungs which frequently results in aspiration pneumonia and death. Also, gels mostly end up in the rumen which has a slower absorption rate than the omasum. This slow rate of absorption necessitates the high levels of calcium chloride in the gels.

Liquid calcium's are orally administered calcium solutions made up of calcium chloride and water. They come in the form of a bottle with a long neck for pouring the liquid into a cow's mouth. As with the gels, the cow is at risk of aspirating the fluid, resulting in pneumonia and death. Liquid calcium also contains a high level of calcium chloride, 150–200 grams in a 300 to 400 cc dose, which can cause acidosis and irritation to the throat. A typical administration of 400 cc's of the liquid calcium also gets the animal excited, which lowers the calcium absorption. These conventional calcium liquids do not contain anything else to help the cow such as vitamins, minerals, carriers to improve the effectiveness of the calcium solution, or an ingredient that makes it taste better.

When these gels and liquids are given to prevent milk fever, the cow tends to lose its appetite, which is not desirable.

It is a general object of this invention to provide a milk fever treatment and preventative for cows which overcomes the limitations and shortcomings of the prior art treatments described above.

It is a further object of this invention to provide a calcium treatment for cows which is easier to administer than prior art treatments.

It is a further object of this invention to provide a calcium treatment for cows which does not cause the cow to lose its appetite and instead stimulates appetite.

It is a further object of this invention to provide a calcium treatment for cows which does not shock the cow's system.

It is a further object of this invention to provide an oral calcium treatment for cows which poses less risk of the substance being inhaled and causing pneumonia than with prior art treatments.

It is a further object of this invention to provide an oral calcium treatment which allows the cow's esophageal groove to open, thereby allowing the composition into the omasum rather than in the rumen.

It is a further object of this invention to provide an oral calcium treatment for cows which excites the cow less than prior art treatments.

It is a further object of this invention to provide an oral calcium treatment for cows which has less risk of causing acidosis than prior art treatments.

It is a further object of this invention to provide an oral calcium treatment for cows which causes less throat irritation than prior art treatments.

It is a further object of this invention to provide an oral calcium treatment for cows which is not administered over the tongue.

It is a farther object of this invention to provide an oral calcium treatment substance for cows which provides other benefits to the cow besides calcium.

It is a further object of this invention to provide an oral calcium treatment substance for cows which tastes better than prior art substances.

It is a further object of this invention to provide an oral calcium treatment substance for cows which can be administered with a drench gun.

BRIEF SUMMARY OF THE INVENTION

The present invention provides a composition for preventing and treating milk fever in freshening cows, and a method of administering that composition. The basic composition is a mixture of water, calcium chloride, propylene glycol, B vitamins and minerals. The calcium chloride content is between 12 and 16%. The propylene glycol is a carrier for the calcium that aids in the dispersion of the calcium into the blood stream and also gives the cow an energy boost and sweetens the taste so that the cow does not object to it as it does to conventional gels and liquids. The B vitamins stimulate the cow's appetite. The minerals help in the absorption of calcium and replace minerals that are used to make the colostrum.

The composition of the present invention is in a liquid form and is preferably administered using a 200 cc drench gun. The end of the dispensing tube of the drench gun is placed between the teeth and cheek of the cow and inserted all the way to the back of the cheek. The end of the dispensing tube has a feature, such as a bend, that ensures the tube is placed between the cheek and teeth and causes a bulge in the cow's cheek which indicates the position of the dispensing tube from outside of the cow's mouth. This position of the dispensing tube allows the cow to swallow a dispensed solution in a near normal manner, which prevents the solution from being inhaled and causing aspiration pneumonia. The minimal irritation of the solution in the cow's throat allows the esophageal groove to open, thereby allowing the liquid into the omasum where absorption is faster than in the rumen where most of the other compositions for this purpose end up. Dosages of a composition of the present invention are, therefore, lower than dosages of other compositions for this purpose.

DETAILED DESCRIPTION

COMPOSITION

Figure 1A:
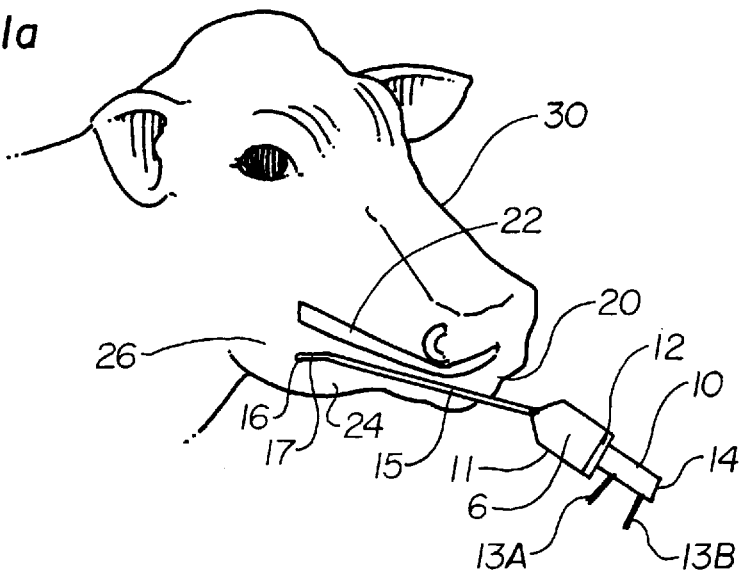
FIG. 1A is an illustration showing the position of the drench gun used to administer the solution in a cow's mouth.

1. Preferred Embodiment.

The present invention provides a low-viscosity liquid composition for preventing and treating milk fever in freshening cows comprised of water, calcium chloride, propylene glycol, magnesium chloride, potassium chloride, riboflavin supplement, vitamin B12 supplement, thiamin HCL, pyridoxine HCL, and D-calcium pantothenate.

The calcium chloride raises the serum calcium in the blood of freshening cows which often have low serum calcium which can lead to milk fever. The amount of calcium chloride in the liquid composition is 5% to 30% by weight (10 to 60 g/200 cc dose), with 12.7% (25.6 g/200 cc's) being preferred. The amount of calcium chloride delivered to the cow is lower than in other calcium solutions, which typically range from 40 to 55 g/per 300–400 cc dose, because the method of administering the liquid of the present invention results in the esophageal groove opening which allows most of the liquid to pass into the omasum where it is absorbed faster than in the rumen where most of the solutions and gels of other treatment methods end up. The lower calcium chloride concentration also has the added benefits of being less likely to cause acidosis and less likely to irritate the cow's throat, which is beneficial for multiple treatments. Chart 1 compares amounts of calcium chloride and calcium per dose of the composition of the present invention and typical gel tubes and liquid calcium supplements.

Chart 1

|  | Present Invention | Liquid Drenches | Gel Tubes |
|---|---|---|---|
| Dose | 200 cc | 300 to 400 cc | 300 cc |
| Calcium Chloride | 75 grams | 150 to 200 grams | 150 to 200 grams |
| Pure Calcium | 25.6 grams | 40–55 grams | 49–55 grams** |

**Gel tubes are also available in 100 grams also, but the majority of tubes that are sold are in the 49–55 grams.

The propylene glycol gives the cow an energy boost and also gives the composition a sweet taste so the cow will swallow it rather than fight it or spit it out. The amount of propylene glycol in the liquid composition ranges from 1% to 25% by weight, with 12.62% being preferred.

The minerals magnesium and potassium replace minerals in the milk and help in the calcium absorption. They are provided in the liquid composition by magnesium chloride and potassium chloride. The amount of magnesium chloride in the liquid composition ranges from 0.05% to 10% by weight, with 1.67% being preferred. The amount of potassium chloride in the liquid composition ranges from 0.01% to 1% by weight with 0.72% being preferred.

Loss of appetite is a common problem with other calcium treatments. A well nourished cow is less likely to develop milk fever, ketosis, displaced abomasum or retained placenta. Five elements to stimulate the cow's appetite are present in the liquid composition. The composition contains riboflavin, vitamin B12, thiamin HCL, pyridoxine HCL and D-calcium pantothenate collectively within a range of 0.005% to 0.1% by weight, and preferably each element is about 0.0239% by weight.

2. First Alternate Embodiment.

The following ingredients are added to a composition of the preferred embodiment:

Amino acid glycine in a range of 0.5 to 10.0% by weight, with 5.0% being preferred, increases the absorption of calcium.

Selenium in a range of 0.1 to 3.0 mg, with 1.5 mg being preferred per 200 cc dose, increases the immune response in a fresh cow.

Cobalt in a range of 7.5 to 750 ppm, with 350 ppm being preferred, to aid in the absorption and use of Vitamin B12.

Magnesium in a range of 0.05 to 10% by weight, with 1.67% preferred, to treat and prevent grass tetany.

A flavor, such as root beer, to improve the taste of the liquid.

Vitamin E in a range of 10 to 10,000 I.U. with 1,000 I.U. being preferred per 200 cc dose, increases the immune response in a fresh cow.

3. Second Alternate Embodiment.

Another composition comprising the ingredients in the quantities listed in Table 1 has been used for prevention and treatment of Ketosis. That composition is prepared and an equal amount of it is mixed with a composition of the preferred embodiment or a composition of the first alternate embodiment. Maximum, minimum and preferred quantities listed are for a 200 cc volume.

dispensing tube 15. The compositions are administered at a rate of about 20 to 50 cc's/second, with the head somewhat raised.

Placement of tube 15 between teeth 22 and cheek 24 of cow 30 and inserting it such that end 16 of dispensing tube 15 is at or near the back 26 of cheek 24 is much less objectionable to cow 30 than when tube 15 is forced between the cow's upper and lower teeth 22. Cow 30 swallows the composition in a near-normal manner thereby nearly eliminating the danger of pneumonia and death from composition being aspirated into cow's lungs. This procedure also does not get cow 30 excited, thereby allowing better absorption and higher blood levels of calcium than are often achieved with more excited cows. This procedure is also very simple for the dairyman to administer to cows.

Figure 2:
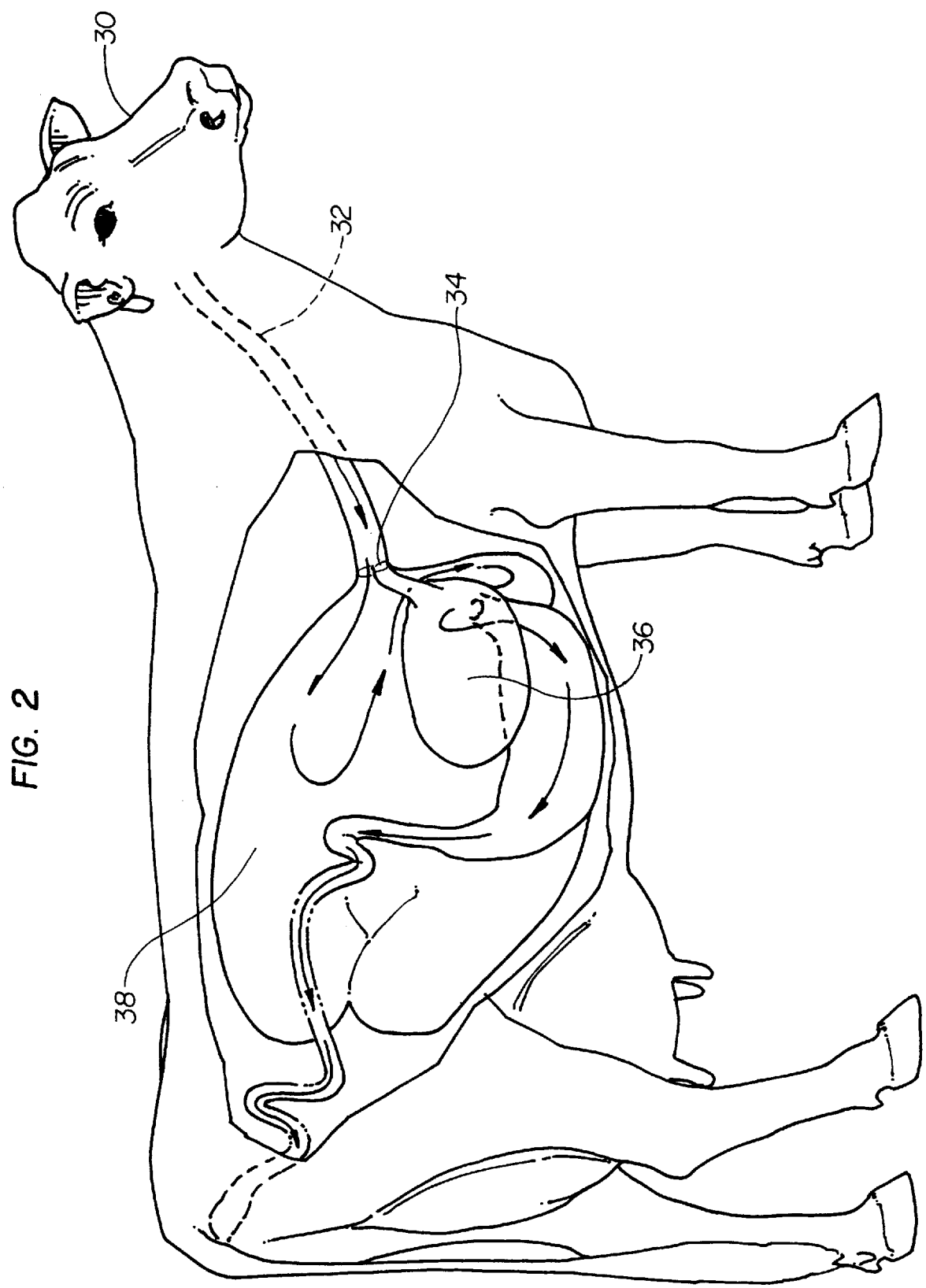
FIG. 2 is an illustration of the digestive system of a cow.

Referring to FIG. 2, a normal swallowing action takes place, and because there is minimal irritation in the esophagus 32, the esophageal groove 34 can open thereby allowing the composition into the omasum 36 rather than in the rumen 38 where most of the other more irritating compositions end up. Absorption of the composition is faster in the omasum 36 than in the rumen 38. This allows for a lower concentration of calcium in the composition of the present invention than in other compositions designed for supplementing calcium orally, but achieves similar results.

TESTING

Blood tests were performed on freshening Jersey cows in Wisconsin, within 2–4 hours of freshening, to determine the effectiveness of the preferred composition and method of

TABLE 1

| INGREDIENT | MAXIMUM | MINIMUM | PREFERRED | PURPOSE |
|---|---|---|---|---|
| Propylene Glycol | 1 g. | 500 g. | 180 g | energy boost |
| Niacin | 5 g. | 14 g. | 10 g. | ketosis treatment |
| Vitamin A | 55,000 I.U. | 900,000 I.U. | 420,000 I.U. | immune stimulant |
| Vitamin B2 | 3 mg | 500 mg | 48 mg | appetite stimulant |
| Vitamin B6 | 4 mg | 200 mg | 60 mg | appetite stimulant |
| Vitamin B12 | 45 Mcg | 1000 Mcg | 600 Mcg | appetite stimulant |
| D-CAL pantothenate | 15 mg | 500 mg | 180 mg | appetite stimulant |
| Folic Acid | 0.5 mg | 20 mg | 2.8 mg | appetite stimulant |
| Vitamin C | 15 mg | 920 mg | 180 mg | immune stimulant |
| Vitamin D3 | 10,000 I.U. | 900,000 I.U. | 84,000 I.U. | help calcium absorb |
| Vitamin E | 5 I.U. | 950 I.U. | 100 I.U. | immune stimulant |

METHOD OF ADMINISTERING COMPOSITIONS

Figure 1B:
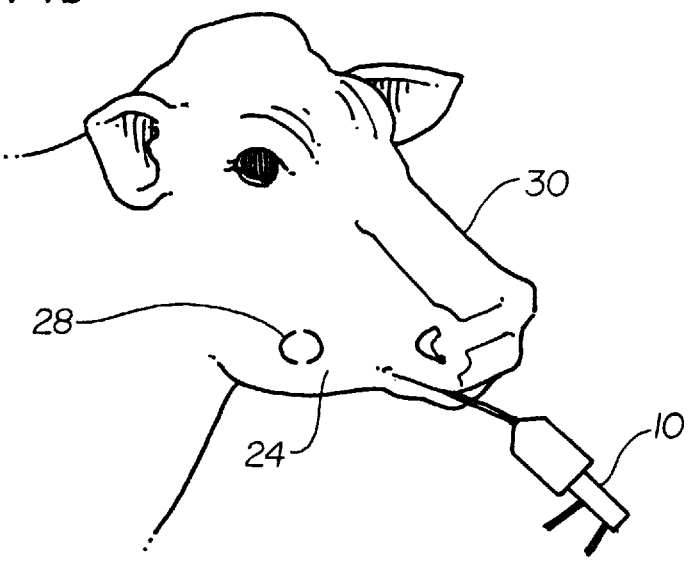
FIG. 1B is an illustration showing the external bulge in the cow's cheek used to locate the position of the drench gun in the cows mouth.

Referring to the drawings, wherein like reference numerals designate like or similar elements throughout, a preferred method of administering compositions of present invention is illustrated in FIGS. 1 and 1A.

Referring to FIG. 1, a drench gun 10 is used to administer compositions of the present invention into the mouth 20 of a cow 30. Drench gun 10 construction is well known in the industry. Preferably a 200 cc model is used for this application. A drench gun 10 loaded with a liquid 6 to be dispensed is positioned in a cow's 30 mouth 20 so that dispensing tube 15 of drench gun 10 is inserted between the teeth 22 and cheek 24. Dispensing tube 15 is placed such that its entire length, generally 7–10 inches, is within the mouth 20 and end 16 of tube 15 is at or near the back 26 of cheek 24. Liquid 6 is dispensed through dispensing tube 15 by manually compressing spring-loaded levers 13A and 13B on handle 14 which pushes piston 12 down cylinder 11 to force liquid 6 out of cylinder 11 and into dispensing tube 15.

Referring to FIGS. 1 and 2, proper location of dispensing tube 15 is evidenced from outside the cow's mouth by observing a bulge 28 in the cheek 24 of the cow 30 caused by a feature, such as a bent section 17, of the end 16 of administering it. Blood samples were drawn from the subject cows just before administering a mixture of the preferred composition, then again 15 minutes and 30 minutes after administering it. The blood samples were analyzed for serum calcium content by the laboratory of Myrtle Worth Medical Center, 2321 Stout Road, Menomonie, Wis. 54751. Table 2 lists the results.

TABLE 2

| Cow Number | Before Administering Solution* | 15 Minutes After Admin.* | 30 Minutes After Admin.* |
|---|---|---|---|
| 32 | 7.6 | 9.6 | 9.8 |
| 69 | 6.3 | 10.1 | 9.8 |
| 10 | 5.9 | 8.3 | 8.1 |
| 66 | 4.6 | 5.8 | 5.8 |
| 40 | 6.0 | 8.0 | 8.5 |
| 44 | 7.9 | 8.8 | 8.9 |
| 77 | 7.4 | 10.5 | 10.8 |
| E | 6.7 | 8.3 | 7.7 |
| 68 | 8.5 | 10.9 | 10.6 |

TABLE 2-continued

| Cow Number | Before Administering Solution* | 15 Minutes After Admin.* | 30 Minutes After Admin.* |
|---|---|---|---|
| 1 | 8.5 | 9.8 | 9.9 |
| 2 | 6.0 | 8.0 | 8.5 |

* = mg of calcium/100 cc of blood
Normal calcium level = 9.0 mg/100 cc of blood
Subclinical calcium level = 7.5 & lower mg/100 cc of blood
Rumen shuts down = 6.0 mg/100 cc of blood
The cow is down at 4.0 mg/100 cc of blood To determine the effectiveness of the preferred composition and method of administering it on a different breed of cow, similar blood tests were performed on freshening Holstein cows in Arizona within 2–4 hours of freshening which were treated with a mixture of the preferred composition. Table 3 lists those results.

TABLE 3

| Cow Number | Before Administering Solution* | 15 Minutes After Admin.* | 30 Minutes After Admin.* |
|---|---|---|---|
| A | 8.2 | 9.4 | 9.6 |
| B | 5.9 | 6.9 | 6.9 |
| C | 6.9 | 8.3 | 8.4 |
| D | 7.0 | 8.9 | 9.3 |
| E | 8.0 | 8.9 | 9.0 |

* = mg of calcium/100 cc of blood
Normal Calcium level = 9.0 mg/100 cc of blood

These tests show that a mixture of the preferred composition administered in the preferred method of this invention is effective at raising serum calcium level to a near normal level in freshening Jersey and Holstein cows within 15 minutes of administration.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. A veterinary composition comprising:
   (a) water;
   (b) an amount of propylene glycol between 1% and 25% by weight;
   (c) an amount of calcium chloride between 5% and 30% by weight; and
   (d) an amount of B vitamins between 0.005% and 0.1% by weight.

2. The composition of claim 1 further comprising an amount of magnesium chloride between 0.05% and 10% by weight and an amount of potassium chloride between 0.01% and 1% by weight.

3. The composition of claim 2 where said amount of said magnesium chloride in the liquid composition is approximately 1.67% by weight.

4. The composition of claim 2 where said amount of said potassium chloride in the liquid composition is approximately 0.72% by weight.

5. The composition of claim 1 where said B vitamins are B12, thiamin, riboflavin, pyridoxine HCL, and D-calcium pantothenate.

6. The composition of claim 5 where said thiamin is in the form of thiamin HCL.

7. The composition of claim 1 where said amount of said calcium chloride is 11% to 16% by weight.

8. The composition of claim 1 where said amount of said propylene glycol is 5% to 10% by weight.

9. The composition of claim 1 where said amount of each of said B vitamins are in the amount of approximately 0.024% by weight.

10. A veterinary composition for preventing and treating milk fever in freshening cows, comprising:
    (a) an amount of water between 50% and 60% by weight;
    (b) an amount of propylene glycol between 1 and 25% by weight;
    (c) an amount of calcium chloride between 5% and 30% by weight;
    (d) an amount of B vitamins between 0.005% to 0.1% by weight, wherein said B vitamins are B12, thiamin. riboflavin, pyridoxine HCL, and D-calcium pantothenate; and
    (e) an amount of magnesium chloride and potassium chloride said amount of magnesium chloride being between 0.05% and 10% by weight and said amount of potassium chloride being between 0.01% and 1% by weight.

11. A low-viscosity liquid composition for quickly and effectively raising serum calcium levels in the blood of a freshening cow to prevent and treat milk fever, the composition comprising:
    (a) an amount of water between 50% and 60% by weight;
    (b) a pharmaceutically effective amount of propylene glycol for sweetening the composition, for providing an energy boost to the freshening cow, and for quickly and effectively dispersing calcium into the freshening cow by opening the cow's esophageal groove, said amount of propylene glycol being between 5% and 10% by weight; and
    (c) a pharmaceutically effective amount of calcium chloride for quickly raising serum calcium levels in the freshening cow, whereby the cow absorbs said amount of calcium chloride in the cow's abomasum, said amount of calcium chloride being between 11% and 16% by weight.

* * * * *